United States Patent
O'Neill

(10) Patent No.: US 11,084,983 B2
(45) Date of Patent: Aug. 10, 2021

(54) FLUIDIZED BED CONVERSION OF OXYGENATES WITH INCREASED AROMATIC SELECTIVITY

(71) Applicant: ExxonMobil Research and Engineering Company, Annandale, NJ (US)

(72) Inventor: Brandon J. O'Neill, Lebanon, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/741,889

(22) Filed: Jan. 14, 2020

(65) Prior Publication Data
US 2020/0239782 A1      Jul. 30, 2020

Related U.S. Application Data

(60) Provisional application No. 62/796,234, filed on Jan. 24, 2019.

(51) Int. Cl.
*C07C 1/24* (2006.01)
*C10G 3/00* (2006.01)
*B01J 29/85* (2006.01)

(52) U.S. Cl.
CPC .............. *C10G 3/49* (2013.01); *B01J 29/85* (2013.01); *C07C 1/24* (2013.01); *C07C 2527/14* (2013.01);
(Continued)

(58) Field of Classification Search
CPC ....... C07C 1/20; C07C 2529/40; C07C 11/02; C07C 2529/70; C07C 2529/65; C07C 2529/85; C07C 15/073; C07C 15/08; C07C 2521/02; C07C 2521/04; C07C 2521/08; C07C 2521/10; C07C 2527/16;
(Continued)

(56) References Cited

U.S. PATENT DOCUMENTS 3,354,078 A    11/1967    Miale et al.
3,894,104 A     7/1975    Chang et al.
(Continued)

FOREIGN PATENT DOCUMENTS

WO    2010011958 A2    1/2010
WO    20180106396 A1   6/2018

OTHER PUBLICATIONS

The International Search Report and the Written Opinion for PCT/US2020/013617 dated Apr. 24, 2020.

*Primary Examiner* — Sharon Pregler
(74) *Attorney, Agent, or Firm* — Liza Negron

(57) ABSTRACT

Systems and methods are provided for conversion of oxygenate-containing feeds to a hydrocarbon effluent that includes a naphtha boiling range portion with an increased research octane number and/or increased octane rating. The conditions for converting the oxygenate-containing feed can correspond to conversion conditions for fluidized bed operation and/or moving bed operation, with a low acidity catalyst that also includes phosphorus to improve the hydrogen transfer rate relative to the expected hydrogen transfer rate for a low acidity catalyst. In addition to providing a naphtha fraction with an improved research octane number and/or octane rating, the amount of durene in the naphtha fraction can be reduced or minimized.

19 Claims, 11 Drawing Sheets

(52) U.S. Cl.
CPC .... *C07C 2529/40* (2013.01); *C10G 2300/305* (2013.01); *C10G 2300/70* (2013.01); *C10G 2400/20* (2013.01); *C10G 2400/30* (2013.01)

(58) Field of Classification Search
CPC ............ C07C 2529/42; C07C 2529/44; C07C 2529/46; C07C 2/12; C07C 2/864; B01J 2229/42; B01J 29/084; B01J 29/18; B01J 29/40; B01J 2229/26; B01J 29/405; B01J 20/183; B01J 2229/18; B01J 29/44; B01J 29/46; B01J 37/0009
See application file for complete search history.

(56) References Cited

U.S. PATENT DOCUMENTS

| | | | |
|---|---|---|---|
| 4,088,706 A | 5/1978 | Kaeding | |
| 4,582,815 A | 4/1986 | Bowes | |
| 5,367,100 A | 11/1994 | Gongwei et al. | |
| 6,506,954 B1 | 1/2003 | Brown et al. | |
| 9,090,525 B2 | 7/2015 | Brown | |
| 10,590,353 B2 * | 3/2020 | McCarthy | C10G 3/49 |
| 2013/0102825 A1 | 4/2013 | Beutel et al. | |
| 2013/0281753 A1 | 10/2013 | McCarthy et al. | |
| 2015/0174561 A1 | 6/2015 | McCarthy et al. | |
| 2015/0174562 A1 | 6/2015 | McCarthy et al. | |
| 2015/0174563 A1 | 6/2015 | McCarthy et al. | |
| 2016/0090332 A1 | 3/2016 | Buchanan et al. | |
| 2016/0102032 A1 | 4/2016 | Du et al. | |
| 2016/0176776 A1 | 6/2016 | Ilias et al. | |
| 2018/0201843 A1 | 7/2018 | O'Neill et al. | |

* cited by examiner

FLUIDIZED BED CONVERSION OF OXYGENATES WITH INCREASED AROMATIC SELECTIVITY

CROSS-REFERENCE TO RELATED APPLICATIONS

This application claims the benefit of U.S. Provisional Application No. 62/796,234, filed on Jan. 24, 2019, the entire contents of which are incorporated herein by reference.

FIELD

This invention relates to fluidized bed processes for forming aromatics by conversion of oxygenates.

BACKGROUND

A variety of industrial processes are known for conversion of low boiling carbon-containing compounds to higher value products. For example, methanol to gasoline (MTG) is a commercial process that produces gasoline from methanol using ZSM-5 catalysts. In the MTG process, methanol is first dehydrated to dimethyl ether. The methanol and/or dimethyl ether then react in a series of reactions that result in formation of aromatic, paraffinic, and olefinic compounds. The resulting product consists of liquefied petroleum gas (LPG) and a high-quality gasoline comprised of aromatics, paraffins, and olefins. The typical MTG hydrocarbon product consists of 40-50% aromatics plus olefins and 50-60% paraffins. It is noted that the aromatics portion of the MTG hydrocarbon product is typically less than 40%, such as 35% or less.

U.S. Pat. No. 3,894,104 describes a method for converting oxygenates to aromatics using zeolite catalysts impregnated with a transition metal. Yields of aromatics relative to the total hydrocarbon product are reported to be as high as 58% with a corresponding total $C_5+$ yield as high as 73%.

U.S. Patent Application Publication 2013/0281753 describes a phosphorous modified zeolite catalyst. The phosphorous modification reduces the change in alpha value for the catalyst after the catalyst is exposed to an environment containing steam. The phosphorous modified catalysts are described as being suitable, for example, for conversion of methanol to gasoline boiling range compounds.

U.S. Patent Application Publications 2015/0174561, 2015/0174562, and 2015/0174563 describe catalysts for conversion of oxygenates to aromatics. The catalysts include a zeolite, such as an MFI or MEL framework structure zeolite, with a supported Group 12 metal on the catalyst.

U.S. Pat. No. 9,090,525 describes conversion of oxygenates in the presence of a zeolitic catalyst to form naphtha boiling range compounds with increased octane. A portion of the naphtha boiling range olefins from an initial conversion product are recycled to the oxygenate conversion process to allow for formation of heavier naphtha boiling range compounds, including aromatics.

U.S. Patent Application Publication 2018/0201843 describes conversion of oxygenates to hydrocarbons using a variable catalyst composition. The conversion is performed under fluidized bed conditions. The composition of the catalyst in the fluidized bed can be varied during the conversion reaction by selecting the type of fresh catalyst introduced into the reactor during the course of operation.

SUMMARY OF THE INVENTION

In some aspects a method for forming a hydrocarbon composition is provided. The method can include exposing an oxygenate-containing feed to conversion catalyst particles including 0.01 wt % to 20 wt % phosphorus on a zeolitic support under effective oxygenate conversion conditions to form a hydrocarbon product comprising $C_{5+}$ hydrocarbons and $C_2$-$C_4$ olefins. The $C_{5+}$ hydrocarbons can have a research octane number of 80 or more and/or an octane rating of 80 or more. The effective oxygenate conversion conditions can optionally correspond to a temperature of 320° C. to 425° C., a pressure of 10 psig (~70 kPa-g) or more, and a weight hourly space velocity of 0.1 hr$^{-1}$ to 10.0 hr$^{-1}$. The exposing can be performed in a reaction system comprising a fluidized bed reactor, a moving bed reactor, a riser reactor, or a combination thereof. In some aspects, the conversion catalyst particles can have an average Alpha value of 8 to 15. Additionally or alternately, in some aspects, the method can further include removing a first portion of catalyst particles from the reaction system. In such aspects, the fresh catalyst particles added to the reaction system to replace the removed first portion of the catalyst particles can have an Alpha value of 8 to 100, such as 15 to 100.

DETAILED DESCRIPTION

Figure 1:
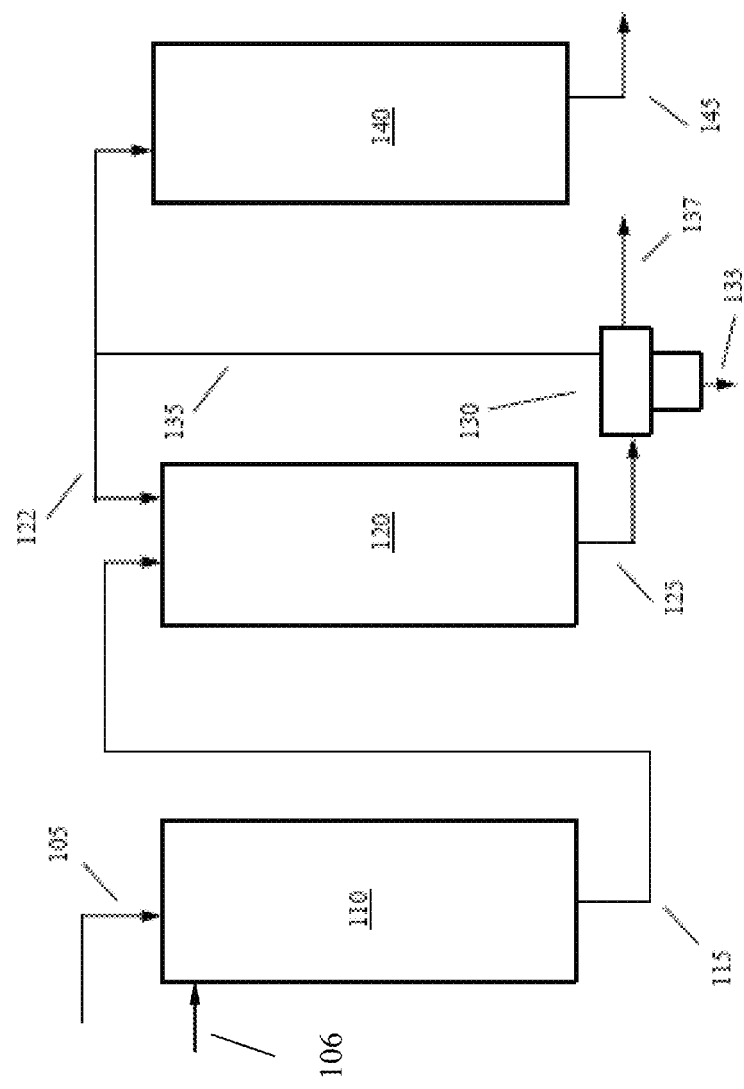
FIG. 1 schematically shows an example of a reaction system including a conversion reactor.

In various aspects, systems and methods are provided for conversion of oxygenate-containing feeds to a hydrocarbon effluent that includes a naphtha boiling range portion with an increased research octane number (RON) and/or increased octane rating (RON+MON/2). The conditions for converting the oxygenate-containing feed can correspond to conversion conditions for fluidized bed and/or moving bed operation, with a low acidity catalyst that also includes phosphorus to improve the hydrogen transfer rate relative to the expected hydrogen transfer rate for a low acidity catalyst. In addition to providing a naphtha fraction with an improved research octane number and/or octane rating, the amount of durene in the naphtha fraction can be reduced or minimized.

Conventionally, methanol to gasoline conversion processes have typically been performed in one of two types of systems. One option has been to perform the conversion process in a fixed bed environment. While this is effective for generally performing the conversion process, the activity of the catalyst cannot be readily controlled. In order to account for this, a fixed bed catalyst can often correspond to a catalyst with a higher Alpha value. For example, in a MTG process in a fixed bed environment, at initial loading, the Alpha value for a phosphorus-containing catalyst can be 100 or more, while a non-phosphorus-containing catalyst may have an Alpha value of 400 or more.

Some loss of catalyst activity can be due to accumulation of coke on the catalyst. Additionally, due to the water generated as a by-product from the methanol conversion, the conversion catalyst is exposed to steaming during the course of the process. This can lead to catalyst deactivation due in part to loss of acidity, such as acidity as characterized via the Alpha value of the catalyst. In a commercial setting, fixed bed processes typically require long run lengths in order to be suitable for use. As a result, the fresh catalyst loaded for a fixed bed reactor can typically have relatively high Alpha values, as noted above. Over time, as a portion of the bed deactivates, a larger percentage of the feed can react with catalyst lower in the bed that has a reduced amount of deactivation. However, as the catalyst deactivates, the exposure of the feed to lower activity catalyst in an upper portion of the bed can also produce a modified product slate that may be less desirable.

Another option is to perform the conversion process in a fluidized bed or moving bed environment. Fluidized bed and/or moving bed processes can allow for continuous regeneration of catalyst during processing as well as continuous removal of spent catalyst and replacement with fresh catalyst, which can allow for improved control over catalyst activity. As a result, it is feasible to perform fluidized bed methanol conversion processes with catalysts having a lower average Alpha value. For example, the average Alpha value can be maintained at a value of 8 to 15, or 10 to 15, with a substantial portion of the catalyst having an Alpha value of roughly 5 to 10, and optionally another portion of the catalyst can have an Alpha value of less than 5. In such aspects, the replacement or fresh catalyst added to the reactor can have an Alpha value of 8 to 100, or 8 to 50, or 10 to 75, or 10 to 50, or 15 to 100, or 15 to 50, or 20 to 75, or 20 to 50, or 8 to 40, or 10 to 40, or 15 to 40, or 20 to 40. It is noted that such Alpha values for the fresh or replacement catalyst can be substantially below the Alpha values for fresh catalyst that would be used in a typical fixed bed environment.

It has been discovered that a conversion effluent including a naphtha boiling range fraction with improved research octane number and/or octane rating can be produced by performing the conversion in a fluidized bed environment with a relatively low acidity catalyst. This can be achieved by performing the conversion of the oxygenate-containing feed using a phosphorus-containing catalyst with both a relatively low average Alpha value and a relatively low maximum Alpha value (i.e., low value for the Alpha of the fresh catalyst). This use of a low Alpha value phosphorus-containing catalyst can unexpectedly allow for production of a naphtha fraction with increased RON and/or octane rating at sustainable commercial production conditions.

Without being bound by any particular theory, it is believed that the unexpected combination of high RON and/or octane rating and low durene content for the naphtha portion of the conversion effluent is due to providing conversion conditions that allow for increased hydrogen transfer when using a low acidity catalyst. The hydrogen transfer activity of a conversion catalyst can be dependent on both the acidic sites of the zeolite portion of the catalyst and the amount of phosphorus present on the catalyst (if any). For a conventional catalyst with an Alpha value of 100 or more, it is believed that the hydrogen transfer activity of the catalyst can be dominated by the activity of the acidic sites on the zeolite. In such an environment, the presence or absence of phosphorus has a reduced impact because of the dominant hydrogen transfer activity provided by the acidic sites. Of course, an Alpha value of 100 or more also indicates that all of the other types of activity associated with acidic sites will also be present. Under such high Alpha value conditions, and in particular with both high Alpha and a phosphorus containing catalyst, the yield of $C_{5+}$ hydrocarbons can be reduced or minimized. A reduced yield of $C_{5+}$ hydrocarbons is not beneficial when attempting to make gasoline.

By contrast, for a conversion catalyst with a lower Alpha value, addition of phosphorus to the catalyst can increase the hydrogen transfer activity for the catalyst without also increasing the other types of activity (such as cracking) associated with the acidic sites. By providing increased hydrogen transfer activity in an otherwise low acidity environment, it has been discovered that the hydrogen transfer activity can unexpectedly cause preferential formation of naphtha boiling range aromatics. This can result in the naphtha boiling range portion of the effluent having a higher RON and/or higher octane rating, as aromatics can be preferentially formed without also causing increased amounts of other reactions (such as cracking) that can remove such high octane components. It is noted that without the increased hydrogen transfer activity provided by phosphorus, conversion of methanol with a low acidity catalyst can tend to produce a lower yield of aromatics, with a corresponding reduction in RON and/or octane rating. Additionally, although the mechanism is not clear, it appears that providing a phosphorus-containing catalyst with low Alpha value can also unexpectedly reduce or minimize formation of durene.

Natural gas, coal, and/or biomass are becoming increasingly important sources of carbon for use in production of fuel and/or lubricant products. A first step in conversion of carbon from a natural gas, coal, and/or biomass source can be a conversion of methane to methanol. Once methanol is formed, various fixed bed, fluid bed, and moving bed processes can be used to convert methanol to higher value products, such as fuels, aromatics, and/or olefins. Such processes can use zeolitic catalysts, such as MFI framework (ZSM-5) zeolitic catalysts. Optionally, the zeolitic catalysts can include a supported transition metal, such as Zn, to provide increased selectivity for a desired product, such as aromatics.

Some difficulties with conversion of methanol to naphtha boiling range products (such as aromatics) for use as gasoline can be related to the tendency for the zeolitic catalyst to deactivate relatively quickly. For zeolitic frameworks other than MFI, the catalyst deactivation can also impact the general ability of the catalyst to convert oxygenates within a feed.

One option for characterizing the lifetime of a catalyst is in terms of the exposure time of the catalyst to oxygenates generally, or to a specific oxygenate such as methanol. The weight of oxygenate exposure per weight of catalyst can be referred to as an amount of catalyst exposure. In an environment where catalyst can be removed and added, the average catalyst exposure corresponds to an average exposure of catalyst to feed across the catalyst in the catalyst inventory of the reaction system.

While the average catalyst exposure can be helpful in characterizing a catalyst, it has been discovered that the temperature and pressure of the exposure is also relevant to determining how the catalyst activity is impacted. In order to take advantage of this discovery, instead of characterizing a catalyst based on average catalyst exposure to an oxygenate, a normalized catalyst exposure can be used that also factors in temperature and pressure. In this discussion, the normalized catalyst exposure at a temperature and pressure is defined as the weight of oxygenate per weight of catalyst that can be converted at the specified temperature and pressure before the oxygenate conversion for the catalyst drops to 99% or less. The amount of oxygenate exposure at the specified temperature and pressure that results in 99% or less oxygenate conversion is defined as having a normalized catalyst exposure of 1.0. Based on this characterization, any amount of oxygenate exposure to the catalyst at the specified temperature and pressure can then be expressed as a normalized catalyst exposure. It has been discovered that naphtha with improved octane and/or reduced durene can be formed by operating a fluidized bed and/or moving bed reactor with catalyst having a normalized average catalyst exposure of 1.0 or less. It is noted that a normalized catalyst exposure can be determined for a specific oxygenate, such as methanol. For example, a normalized methanol catalyst exposure is defined as the amount of methanol that a catalyst can convert at a specified temperature and pressure before the methanol conversion for the catalyst drops to 99% or less.

In this discussion, octane rating is defined as (RON+MON)/2, where RON is research octane number and MON is motor octane number. For values reported in the examples below, RON and MON values were determined based on a published model that determines octane ratings for a blend of components based to determine a blended octane. The model is described at Ind Eng Chem Res 2006, 45, 337-345. The model is believed to correlate with experimentally determined values. In the claims below, Research Octane Number (RON) is determined according to ASTM D2699. Motor Octane Number (MON) is determined according to ASTM D2700.

In this discussion, the naphtha boiling range is defined as 50° F. (~10° C., roughly corresponding to the lowest boiling point of a pentane isomer) to 350° F. (177° C.). The distillate fuel boiling range, is defined as 350° F. (177° C.) to 700° F. (371° C.). Compounds ($C_{4-}$) with a boiling point below the naphtha boiling range can be referred to as light ends. It is noted that due to practical considerations during fractionation (or other boiling point based separation) of hydrocarbon-like fractions, a fuel fraction formed according to the methods described herein may have T5 and T95 distillation points corresponding to the above values (or T10 and T90 distillation points), as opposed to having initial/final boiling points corresponding to the above values. While various methods are available for determining boiling point information for a given sample, for the claims below ASTM D86 is a suitable method for determining distillation points (including fractional weight distillation points) for a composition.

Feedstocks and Products—Oxygenate Conversion

In various aspects, catalysts described herein can be used for conversion of oxygenate feeds to aromatics and/or olefins products, such as oxygenates containing at least one $C_1$-$C_4$ alkyl group and/or other oxygenates. Examples of suitable oxygenates include feeds containing methanol, dimethyl ether, $C_1$-$C_4$ alcohols, ethers with $C_1$-$C_4$ alkyl chains, including both asymmetric ethers containing $C_1$-$C_4$ alkyl chains (such as methyl ethyl ether, propyl butyl ether, or methyl propyl ether) and symmetric ethers (such as diethyl ether, dipropyl ether, or dibutyl ether), or combinations thereof. It is noted that oxygenates containing at least one $C_1$-$C_4$ alkyl group are intended to explicitly identify oxygenates having alkyl groups containing 4 carbons or less. Preferably the oxygenate feed can include at least 30 wt % of one or more suitable oxygenates, or at least 50 wt %, or at least 75 wt %, or at least 90 wt %, or at least 95 wt %. Additionally or alternately, the oxygenate feed can include at least 50 wt % methanol, such as at least 75 wt % methanol, or at least 90 wt % methanol, or at least 95 wt % methanol. In particular, the oxygenate feed can include 30 wt % to 100 wt % of oxygenate (or methanol), or 50 wt % to 95 wt %, or 75 wt % to 100 wt %, or 75 wt % to 95 wt %. The oxygenate feed can be derived from any convenient source. For example, the oxygenate feed can be formed by reforming of hydrocarbons in a natural gas feed to form synthesis gas ($H_2$, $CO$, $CO_2$), and then using the synthesis gas to form methanol (or other alcohols). As another example, a suitable oxygenate feed can include methanol, dimethyl ether, or a combination thereof as the oxygenate.

In addition to oxygenates, a feed can also include diluents, such as water (in the form of steam), nitrogen or other inert gases, and/or paraffins or other non-reactive hydrocarbons. In some aspects, the source of olefins can correspond to a low purity source of olefins, so that the source of olefins corresponds to 20 wt % or less of olefins. In some aspects, the portion of the feed corresponding to components different from oxygenates and olefins can correspond to 1 wt % to 60 wt % of the feed, or 1 wt % to 25 wt %, or 10 wt % to 30 wt %, or 20 wt % to 60 wt %. Optionally, the feed can substantially correspond to oxygenates and olefins, so that the content of components different from oxygenates and olefins is 1 wt % or less (such as down to 0 wt %).

In some aspects, such as aspects related to oxygenate conversion to produce gasoline using an MFI or MEL framework catalyst (or potentially another suitable zeolite framework including 10-member rings), the yield of aromatics relative to the total hydrocarbon product can be 25 wt % to 60 wt %, or 38 wt % to 60 wt %, or 40 wt % to 52 wt %, or 38 wt % to 45 wt %. For example, the yield of aromatics relative to the total hydrocarbon product can be at least 25 wt %, or at least 38 wt %, or at least 40 wt %, or at least 45 wt %. Additionally or alternately, the yield of aromatics relative to the total hydrocarbon product can be 60 wt % or less, or 55 wt % or less, or 52 wt % or less, or 50 wt % or less. In various aspects, the yield of olefins relative to the total hydrocarbon product can be 2.0 wt % to 30 wt %, or 2.0 wt % to 25 wt %, or 5.0 wt % to 20 wt %, or 10 wt % to 20 wt %. For example, the yield of olefins relative to the total hydrocarbon product can be at least 2.0 wt %, or at least 5.0 wt %, or at least 10 wt %. Additionally or alternately, the yield of olefins relative to the total hydrocarbon product can be 30 wt % or less, or 25 wt % or less, or 20 wt % or less. In various aspects, the yield of paraffins relative to the total hydrocarbon product can be 20 wt % to 45 wt %, or 20 wt % to 35 wt %, or 25 wt % to 45 wt %, or 25 wt % to 40 wt %. For example, the yield of paraffins relative to the total hydrocarbon product can be at least 20 wt %, or at least 25 wt %, or at least 30 wt % and/or the yield of paraffins relative to the total hydrocarbon product can be 45 wt % or less, or 40 wt % or less, or 35 wt % or less. In the claims below, the relative amounts of paraffins, olefins, and aromatics in a sample can be determined based on ASTM D6839. For the paraffins and olefins generated during oxygenate conversion, at least 50 wt % of the olefins can correspond to $C_3$ and $C_4$ olefins and/or at least 50 wt % of the paraffins can correspond to $C_3$ and $C_4$ paraffins. Additionally or alternately, less than 10 wt % of the paraffins can correspond to $C_1$ paraffins (methane).

The total hydrocarbon product in the conversion effluent can include a naphtha boiling range portion, a distillate fuel boiling range portion, and a light ends portion. Optionally but preferably, the conversion effluent can include less than 1.0 wt % of compounds boiling above the distillate fuel boiling range (371° C.+), such as having a final boiling point of 371° C. or less. In various aspects, the selectivity for forming/yield of a naphtha boiling range portion can be at least 35 wt % and/or 75 wt % or less. For example, the selectivity for forming/yield of a naphtha boiling range portion can be 35 wt % to 75 wt %, or 40 wt % to 65 wt %, or 40 wt % to 60 wt %, or 45 wt % to 70 wt %.

The naphtha boiling range portion formed from a conversion process can have an octane rating (RON+MON/2) of at least 80, or at least 90, or at least 95, or at least 97, or at least 100, or at least 102, or at least 105, such as up to 110. In particular, in aspects involving an MFI or MEL framework catalyst, the octane rating can be 85 to 110, or 95 to 110, or 97 to 110, or 100 to 110. Additionally or alternately, the naphtha boiling range portion can have an RON of 80 to 110, or 85 to 110, or 90 to 110, or 95 to 110, or 97 to 110.

The conversion conditions can also result in generation of CO and/or $CO_2$. In some aspects, the amount of combined CO, $CO_2$, and $CH_4$ can correspond to 6.0 wt % or less of the total hydrocarbon product in a conversion effluent, or 5.0 wt % or less. In this discussion and the claims below, the amounts of CO and $CO_2$ in a conversion effluent are included when determining the amount of the total hydrocarbon product (such as the weight of the total hydrocarbon product).

Suitable and/or effective conditions for performing a conversion reaction to form a naphtha product with increased octane and/or reduced durene can include average reaction temperatures of 320° C. to 425° C. (or 330° C. to 400° C.), total pressures between 10 psig (~70 kPag) to 400 psig (~2700 kPag), or 50 psig (~350 kPag) to 150 psig (~1050 kPag), or 80 psig (~550 kPag) to 120 psig (~800 kPag), and an oxygenate space velocity between 0.1 $h^{-1}$ to 10 $h^{-1}$ based on weight of oxygenate relative to weight of catalyst.

Optionally, a portion of the conversion effluent can be recycled for inclusion as part of the feed to the conversion reactor. For example, at least a portion of the light ends from the conversion effluent can be recycled as part of the feed. The recycled portion of the light ends can correspond to any convenient amount. For example, the amount of recycle can correspond to a ratio of recycled light gas to fresh methanol of 0.2-1.0, or 0.4-1.0. Recycling of light ends can provide olefins, which can serve as an additional reactant in the conversion reaction, as well as providing a mechanism for temperature control.

Various types of reactors can provide a suitable configuration for performing a conversion reaction. Suitable reactors can include moving bed reactors (such as riser reactors), and fluidized bed reactors. It is noted that the activity and/or selectivity of a catalyst for oxygenate conversion can vary as the catalyst is exposed to increasing amounts of oxygenate feed. Conventionally, it has been believed that this modification of the catalyst activity was due primarily to the formation of coke on the catalyst. Under such conventional understanding, when full regeneration is performed on a catalyst (less than 0.1 wt % average coke remaining on the regenerated catalyst), the average catalyst exposure for the regenerated catalyst would typically defined to be zero for purposes of determining average catalyst exposure for catalyst within the reactor. However, it has been discovered that due to exposure to steam in the reaction environment, deactivation due to loss of acidity (such as acidity as measured by Alpha value) can also substantially impact the octane number and/or durene content of the naphtha in the conversion effluent.

With regard to coke, the modification of the catalyst activity and/or selectivity with increasing average catalyst exposure can be reversed at least in part by regenerating the catalyst. In some aspects, a full regeneration can be performed on a catalyst, so that the average amount of coke present on the regenerated catalyst is less than 0.1 wt %. In other aspects, a partial regeneration can be performed, so that the average amount of coke present on the regenerated catalyst after regeneration is greater than 0.1 wt %. The average amount of coke present on a catalyst sample can be readily determined by thermogravimetric analysis. During partial regeneration, the amount of coke on a regenerated catalyst can correspond to 0.1 wt % to 25 wt % relative to the weight of the catalyst. For example, the amount of coke on regenerated catalyst can be 0.1 wt % to 10 wt % relative to the weight of the catalyst, or 1.0 wt % to 25 wt %.

In aspects where a catalyst can be withdrawn from the reactor for regeneration and recycle during operation of the reactor, such as a moving bed reactor and/or fluidized bed reactor, catalyst can be withdrawn and replaced with make-up (fresh) and/or regenerated catalyst. It is noted that withdrawing catalyst from the reactor for regeneration is distinct from removing catalyst entirely from the reaction system and replacing the removed catalyst with fresh make-up catalyst. In this discussion, when full regeneration is performed on a catalyst (less than 0.1 wt % average coke remaining on the regenerated catalyst), the average catalyst exposure for the regenerated catalyst is defined to be zero for purposes of determining average catalyst exposure for catalyst within the reactor. In such aspects when full regeneration is being performed, the average catalyst exposure for catalyst being exposed to oxygenate can be determined based on a) the flow rate of oxygenate into the reactor relative to the amount of catalyst in the reactor, and b) the average residence time of the catalyst in the reactor. These values can allow for a determination of the average grams of oxygenate exposed to the catalyst per gram of catalyst in the reactor (i.e., the average catalyst exposure).

In a moving bed reactor, the residence time for catalyst can correspond to the amount of time required for a catalyst particle to travel the length of the bed to the exit, based on the average velocity of the moving bed. As an example, the flow of methanol into a moving bed reactor can correspond to a space velocity of 1.0 $hr^{-1}$, which means 1 g of methanol per g of catalyst per hour. In such an example, if the average residence time for catalyst in the reactor is 48 hours (based on the average velocity of the moving bed relative to the size of the bed), one of skill in the art would expect a distribution of catalyst exposures within the reactor. The average catalyst exposure for this distribution can roughly be approximated based on the average of a) the catalyst exposure for new catalyst entering the reactor and b) the catalyst exposure for catalyst exiting the reactor. For catalyst that is completely regenerated and/or fresh catalyst, the catalyst exposure when entering the reactor is defined as 0. In this example, the catalyst exposure for the catalyst already present in the reactor is 48 g of methanol per g of catalyst. Thus, for this example, the average catalyst exposure for catalyst in the moving bed would be 24 g of methanol per g of catalyst. This value also corresponds to the amount of catalyst exposure the catalyst receives during the residence time within the reactor. Similarly, in aspects involving a fluidized bed, the catalyst residence time can be determined based on the rate of removal of catalyst from the reactor for regeneration. The catalyst residence time can correspond to the amount of time required to remove an amount of catalyst that is equivalent to the weight of the catalyst bed. Based on that residence time, the average catalyst exposure can be calculated in a similar manner to the calculation for a moving bed.

During a partial regeneration, a catalyst can be exposed to an oxidizing environment for removal of coke from the catalyst, but the net amount of coke remaining on the catalyst after partial regeneration can be greater than 0.1 wt %. When a partial regeneration is performed, the effective average catalyst exposure for the catalyst after regeneration will be a value other than zero, due to the amount of remaining coke on the catalyst. When a partial regeneration is performed, the amount of coke removal can roughly scale in a linear manner with the effective average catalyst exposure of the partially regenerated catalyst. In this discussion and the claims below, when a catalyst is partially regenerated, the average catalyst exposure for the partially regenerated catalyst is determined by multiplying the average catalyst exposure prior to regeneration by the wt % of coke remaining on the catalyst after partial regeneration. As an example, a hypothetical catalyst may have an exposure time of 100 g methanol per g catalyst prior to regeneration. In this example, partial regeneration is used to remove 60 wt % of the coke on the catalyst. This means that 40 wt % (or 0.4 expressed as a fraction) of the coke remains on the catalyst after regeneration. In such an example, the average catalyst exposure for the regenerated catalyst would be 0.4×100=40 g methanol per g catalyst.

In aspects where partial regeneration is performed, the calculation for the average catalyst exposure for catalyst in the reactor can be modified based to account for the fact that any recycled catalyst will have a non-zero initial value of catalyst exposure. The same calculation described above can be used to determine an initial value. The non-zero catalyst exposure for the regenerated catalyst can then be added to the initial value to determine the average catalyst exposure within the reactor. In the example noted above, if the average catalyst exposure for partially regenerated catalyst is 10 g methanol per g catalyst, and if the amount of average exposure within the reactor is 24 g methanol per g catalyst as calculated above, then the average catalyst exposure for the system when using partial regeneration would be 34 g methanol per g catalyst. It is also noted that a portion of the catalyst introduced into a reactor may correspond to fresh make-up catalyst instead of partially regenerated catalyst. In such aspects, the catalyst exposure for the catalyst introduced into the reactor can be a weighted average of the fresh make-up catalyst (zero exposure time) and the catalyst exposure for the partially regenerated catalyst.

For a catalyst including an MFI framework zeolite, the catalyst recycle rate can be dependent on the desired products, with catalyst recycle rates that produce an average catalyst exposure/average cycle length for catalyst in the reactor of about 1 g $CH_3OH$/g catalyst to about 250 g $CH_3OH$/g catalyst potentially being suitable, or about 20 g $CH_3OH$/g catalyst to about 200 g $CH_3OH$/g catalyst, or about 1 g $CH_3OH$/g catalyst to about 150 g $CH_3OH$/g catalyst, or about 20 g $CH_3OH$/g catalyst to about 100 g $CH_3OH$/g catalyst. The target average catalyst exposure can be dependent on the specific nature of the catalyst and/or the desired product mix. The above average catalyst exposures can be achieved, for example, by withdrawing about 0.01 wt % to about 3.0 wt % of catalyst per 1 g of methanol exposed to a g of conversion catalyst, or about 0.01 wt % to about 1.5 wt %, or about 0.1 wt % to about 3.0 wt %, or about 1.0 wt % to about 3.0 wt %. It is noted that these withdrawal rates could be modified, for example, if only a partial regeneration is performed on withdrawn catalyst.

With regard to loss of acidity due to steaming, the acidity of the catalyst can be controlled based on replacement of the catalyst in the reactor via introduction of fresh catalyst. The rate of removal and corresponding rate of introduction of fresh catalyst can be selected to maintain a desired Alpha value for the catalyst in the reactor. It is noted that withdrawing catalyst from the reactor for regeneration is distinct from removing catalyst entirely from the reaction system and replacing the removed catalyst with fresh make-up catalyst.

Conventionally, fresh (or other) make-up catalyst is typically added to a reaction system at a relatively low rate, such as roughly 0.03 wt % of the total catalyst in the reaction system per day. In addition to being sufficient to replace catalyst losses due to attrition, this replacement rate can also be sufficient to maintain the average Alpha value of the catalyst in a desired range. For example, the catalyst replacement rate can be sufficient to maintain an average Alpha value of 10-20, or 10-15, for the catalyst in the reaction system, with 40 wt % or more of the catalyst in the reaction system having an Alpha value of less than 10, or 50 wt % or more, or 60 wt % or more, such as up to 80 wt % or possibly still higher. Additionally or alternately, 1.0 wt % or more (or 3.0 wt % or more, or 5.0 wt % or more, such as up to 10 wt %) of the catalyst in the reaction system can have an Alpha value of less than 5.0, or 4.0 or less, or 3.0 or less. Further additionally or alternately, the Alpha value for the fresh catalyst introduced as part of the replacement rate can be 8 to 100, or 8 to 50, or 10 to 75, or 10 to 50, or 15 to 100, or 15 to 50, or 20 to 75, or 20 to 50, or 8 to 40, or 10 to 40, or 15 to 40, or 20 to 40.

Catalysts for Oxygenate Conversion

In various aspects, a phosphorus-enhanced zeolite catalyst composition can be used for conversion of oxygenate feeds to naphtha boiling range fractions and olefins. Optionally, the catalyst composition can be further enhanced with a transition metal. In this discussion and the claims below, a zeolite is defined to refer to a crystalline material having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", 6$^{th}$ revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework. Thus, "zeolites" as defined herein can include structures such as SAPO and AlPO crystalline frameworks.

A suitable zeolite can include a 10-member or 12-member ring pore channel network, such as a 3-dimensional 10-member ring pore channel. Examples of suitable zeolites having a 3-dimensional 10-member ring pore channel network include zeolites having an MFI or MEL framework, such as ZSM-5 or ZSM-11. ZSM-5 is described in detail in U.S. Pat. Nos. 3,702,886 and Re. 29,948. ZSM-11 is described in detail in U.S. Pat. No. 3,709,979. In some aspects, a zeolite with a 3-dimensional pore channel can be preferred for conversion of methanol, such as a zeolite with an MFI framework. More generally, non-limiting examples of suitable frameworks include framework codes MRE, MTW, TON, MTT, MFI, MEL, BEA, FAU, and CON. Additionally or alternately non-limiting examples of suitable zeolites include ZSM-5, ZSM-11, ZSM-12, ZSM-22, ZSM-23, ZSM-48, beta, USY, and CIT-1.

Generally, a zeolite having desired activity for methanol conversion can have a silicon to aluminum molar ratio of 10 to 200, or 15 to 100, or 20 to 80, or 20 to 40. For example, the silicon to aluminum ratio can be at least 10, or at least 20, or at least 30, or at least 40, or at least 50, or at least 60. Additionally or alternately, the silicon to aluminum ratio can be 300 or less, or 200 or less, or 100 or less, or 80 or less, or 60 or less, or 50 or less.

The catalyst compositions employed herein can further be characterized based on activity for hexane cracking, or Alpha value. Alpha value is a measure of the acid activity of a zeolite catalyst as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst.

It is noted that the molar ratio described herein is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit. Thus, a silicon to aluminum ratio of 10 corresponds to a silica to alumina ratio of 20.

In some aspects, a zeolite in a catalyst can be present at least partly in the hydrogen form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of 400° C. to 700° C. to convert the ammonium form to the active hydrogen form.

Additionally or alternately, a zeolitic catalyst can include and/or be enhanced by a transition metal. Preferably the transition metal is a Group 12 metal from the IUPAC periodic table (sometimes designated as Group IIB), and more preferably the transition metal is Zn. The transition metal can be incorporated into the zeolite/catalyst by any convenient method, such as by impregnation, by ion exchange, by mulling prior to extrusion, and/or by any other convenient method. After impregnation or ion exchange, the transition metal-enhanced catalyst can be treated in air or an inert atmosphere at a temperature of 400° C. to 700° C. The amount of transition metal can be expressed as a weight percentage of metal relative to the total weight of the catalyst (including any zeolite and any binder). A catalyst can include 0.05 wt % to 20 wt % of one or more transition metals, or 0.1 wt % to 10 wt %, or 0.1 wt % to 5 wt %, or 0.1 wt % to 2.0 wt %. For example, the amount of transition metal can be at least 0.1 wt % of transition metal, or at least 0.25 wt % of transition metal, or at least 0.5 wt %, or at least 0.75 wt %, or at least 1.0 wt %. Additionally or alternately, the amount of transition metal can be 20 wt % or less, or 10 wt % or less, or 5 wt % or less, or 2.0 wt % or less, or 1.5 wt % or less, or 1.2 wt % or less, or 1.1 wt % or less, or 1.0 wt % or less.

For a phosphorus-enhanced zeolitic catalyst, the phosphorus can be added by impregnation, ion exchange, mulling prior to extrusion, or another convenient method. Such a catalyst can include 0.01 wt % to 20 wt % of phosphorus, or 0.1 wt % to 20 wt %, or 0.01 wt % to 0.5 wt %, or 0.1 wt % to 5.0 wt %, or 0.01 wt % to 2.0 wt %, or 0.1 wt % to 2.0 wt %.

A catalyst composition can employ a phosphorus-enhanced zeolite in its original crystalline form or after formulation into catalyst particles, such as by extrusion or spray drying. Preferably, the transition metal can be incorporated after formulation of the zeolite to form self-bound catalyst particles. Optionally, a self-bound catalyst can be steamed after extrusion. The terms "unbound" and "self-bound" are intended to be synonymous and mean that the present catalyst composition is free of any of the inorganic oxide binders, such as alumina or silica, frequently combined with zeolite catalysts to enhance their physical properties.

As an alternative to forming self-bound catalysts, zeolite crystals can be combined with a binder to form bound catalysts. Suitable binders for zeolite-based catalysts can include various inorganic oxides, such as silica, alumina, zirconia, titania, silica-alumina, cerium oxide, magnesium oxide, yttrium oxide, or combinations thereof. Additionally or alternately, natural and/or synthetic clays can also be used as at least a portion of the binder. For catalysts including a binder, the catalyst can comprise at least 10 wt % zeolite, or at least 30 wt %, or at least 50 wt %, such as up to 90 wt % or more. Generally, a binder can be present in an amount between 1 wt % and 90 wt %, for example between 5 wt % and 40 wt % of a catalyst composition. In some aspects, the catalyst can include at least 5 wt % binder, such as at least 10 wt %, or at least 20 wt %. Additionally or alternately, the catalyst can include 90 wt % or less of binder, such as 50 wt % or less, or 40 wt % or less, or 35 wt % or less. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

To form a transition metal-enhanced catalyst, a bound catalyst can be impregnated via incipient wetness with a solution containing the desired metal for impregnation, such as Zn or P. The impregnated crystal can then be dried overnight at 250° F. (121° C.), followed by calcination in air for 3 hours at 1000° F. (538° C.). More generally, a transition metal can be incorporated into the zeolitic catalyst at any convenient time, such as before or after ion exchange to form H-form crystals, or before or after formation of a bound extrudate. In some aspects that are preferred from a standpoint of facilitating manufacture of a bound zeolite catalyst, the transition metal can be incorporated into the bound catalyst (such as by impregnation or ion exchange) after formation of the bound catalyst by extrusion or another convenient method.

Example of Reaction System Configuration

FIG. 1 shows an example of a reaction system configuration for performing oxygenate conversion to form a naphtha boiling range product. The reactors shown in FIG. 1 can correspond to moving bed reactors and/or fluidized bed reactors and/or another type of reactor configuration where catalyst can be introduced into catalyst inventory and removed from catalyst inventor while feed is being processed in the reactor. The reactors in FIG. 1 are shown as downflow reactors for convenience, and in other aspects the reactors can have any convenient configuration, such as an upflow configuration. In FIG. 1, a feed 105 can correspond to an oxygenate-containing feed. Optionally, oxygenate feed 105 can be introduced into a reactor as a plurality of input flows, such as a first input flow containing a mixture of methanol and water and a second input flow containing a mixture of nitrogen and hydrogen.

The feed 105 can optionally be introduced into an initial dehydration reactor 110. Initial dehydration reactor 110 can include an acidic catalyst, such as an acidic alumina catalyst, that can facilitate an equilibrium reaction between methanol, water, and dimethyl ether. This can result in production of an effluent 115 that includes both methanol and dimethyl ether. Those of skill in the art will recognize that dimethyl ether and methanol can often be used in similar manners when performing an oxygenate conversion reaction. The dehydration of methanol to form dimethyl ether is highly exothermic. By performing an initial dehydration, the amount of heat generated in the conversion reactor(s) can be reduced, which can allow for improved temperature control in the conversion reactor. Optionally, a portion of the oxygenate feed 105 can bypass the dehydration reactor and can be input directly into conversion reactor 120. In aspects where other oxygenates are used as a feed, such as $C_{2+}$ alcohols or larger ethers, dehydration reactor can be omitted so that feed 105 (or a combination of oxygenate feed 105 and olefinic feed 106) is an input flow for conversion reactor 120.

The oxygenate feed 105 (and/or the effluent 115 containing both dimethyl ether and methanol) can then be passed into conversion reactor 120. The input to conversion reactor 120 can be exposed to a conversion catalyst under effective conditions for forming a conversion effluent 125. The conversion effluent 125 can then be separated, such as by using a 3 phase separator 130. One phase generated by separator 130 can be an aqueous phase 133 that includes a substantial majority of the water present within the conversion effluent 125. Another phase generated by separator 130 can correspond to a hydrocarbon liquid product 137. The hydrocarbon liquid product can correspond to naphtha boiling range compounds formed during the conversion reaction. Optionally, the hydrocarbon liquid product can include a portion of hydrocarbon-like compounds that include one or more heteroatoms, such as oxygen, sulfur, nitrogen, and/or other heteroatoms that are commonly found in petroleum or bio-derived feeds.

A third phase generated by separator 130 can correspond to a hydrocarbon gas product 135. The hydrocarbon gas product 135 can include $C_{4-}$ compounds corresponding to light paraffins and light olefins. Optionally, a recycle portion 122 of hydrocarbon gas product 135 can be recycled as part of the input flows to conversion reactor 120. In some configurations where the amount of recycle portion 122 is sufficiently large, a bleed or waste flow (not shown) can also be present to reduce or minimize the build-up of $C_{4-}$ paraffins in conversion reactor 120.

EXAMPLES—CATALYST

The conversion catalysts used in the following examples correspond to MFI framework (ZSM-5) zeolites bound with silica-alumina clay. The weight ratio of zeolite to binder was 40 wt % to 60 wt %. The ZSM-5 had a silicon to aluminum ratio of 20 to 40. The Alpha value of the catalysts as formulated is described in the Examples below. For phosphorus-enhanced and transition metal-enhanced catalysts, Zn and/or P were added via aqueous impregnation of $Zn(NO_3)_2$ and $H_3PO_4$, respectively. The phosphorus-enhanced catalysts included 4.0 wt % P. The zinc-enhanced catalysts included 0.5 wt % Zn.

A first catalyst corresponded to 40 wt % ZSM-5/60 wt % binder, with a crystal size less than 100 nm. The catalyst was steamed to an Alpha value of roughly 10 prior to use. This was believed to correspond to an equilibrium Alpha value representing long exposure to a steam environment. A second catalyst corresponded to another 40 wt % ZSM-5/60 wt % binder catalyst, but with a crystal size larger than 100 nm. Steaming was used to achieve various levels of Alpha value prior to use. In the examples below, unless otherwise indicated, the first catalyst does not include added phosphorus. In the examples below, unless otherwise indicated, the second catalyst includes 4.0 wt % phosphorus, relative to the weight of the bound catalyst particles.

Example 1—Methanol Conversion in Fluidized Bed Using P-ZSM-5

A series of fluidized bed tests of activity were performed using various ZSM-5 and phosphorus-enhanced ZSM-5 catalysts. The tests were performed at total pressures of 80-120 psig (~550-830 kPa-g) and temperatures of 340° C.-370° C. In some tests, the light ends from the reactor effluent were recycled to allow for inclusion of $C_{4-}$ olefins in the reaction environment. (A purge stream was used to prevent build-up of light paraffins.) For FIGS. 2 to 4, both the first catalyst and the second catalyst were steamed to have an Alpha value of roughly 10.

Figure 2:
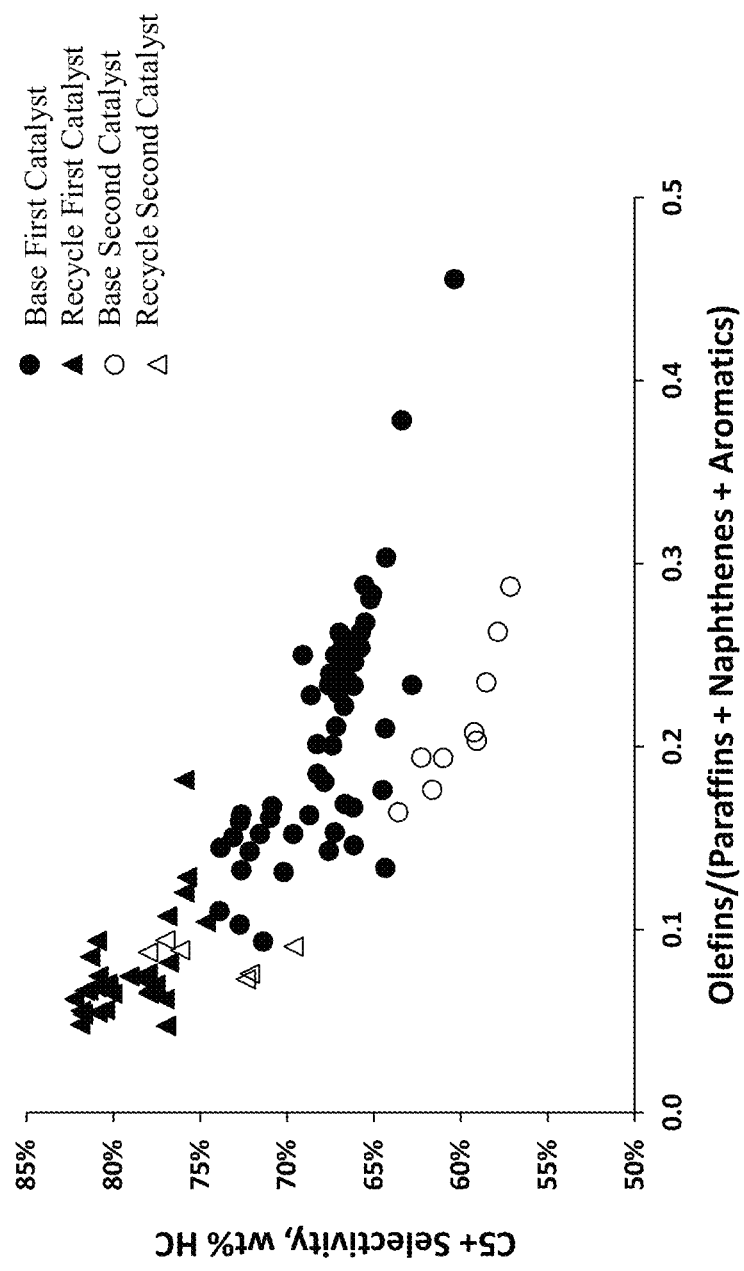
FIG. 2 shows $C_{5+}$ yield versus the fraction of olefins in the total hydrocarbon product from conversion of methanol in the presence of various catalysts.
Figure 3:
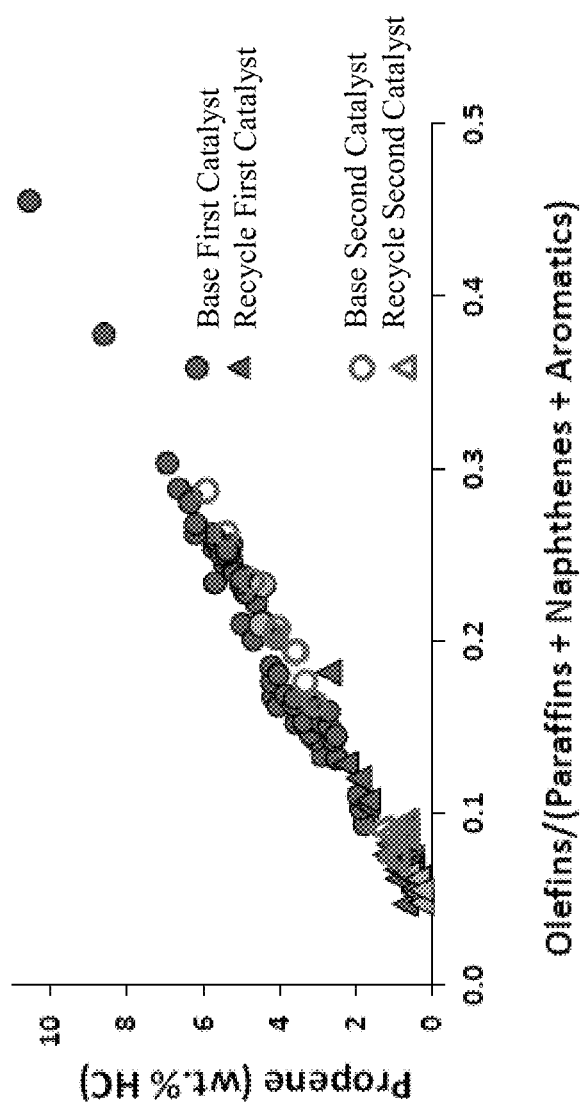
FIG. 3 shows propene yield versus the fraction of olefins in the total hydrocarbon product from conversion of methanol in the presence of various catalysts.
Figure 4:
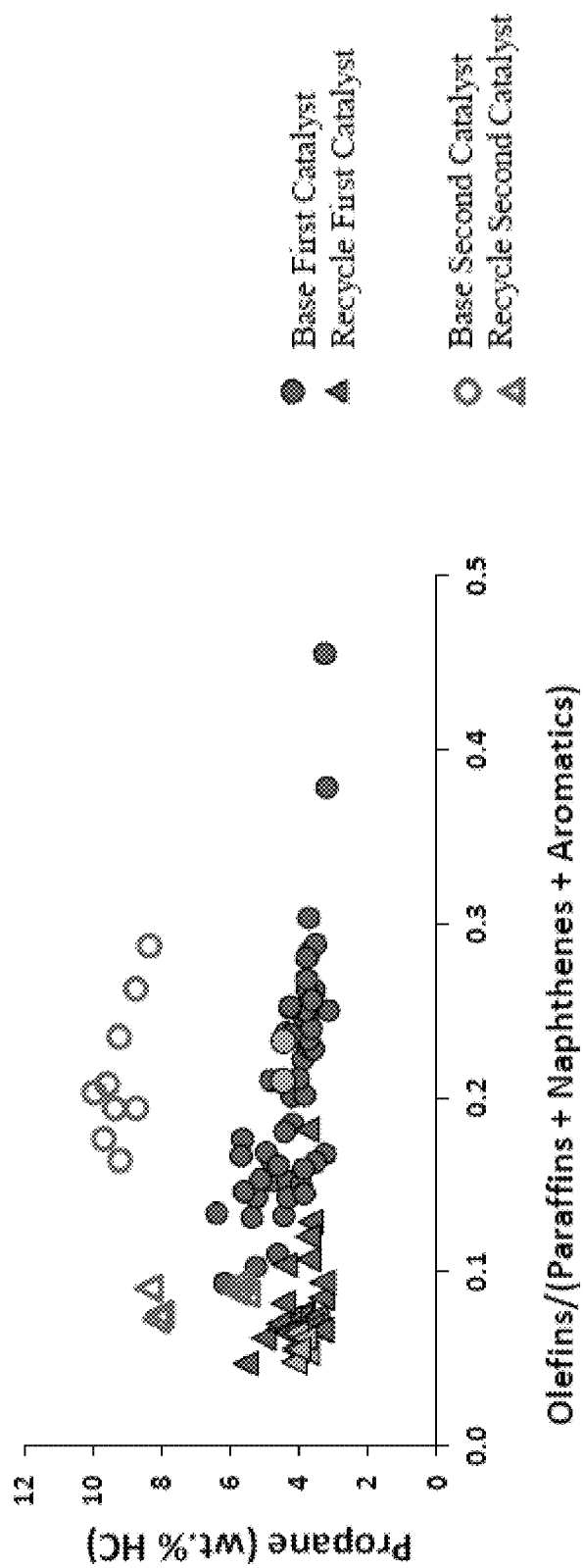
FIG. 4 shows propane yield versus the fraction of olefins in the total hydrocarbon product from conversion of methanol in the presence of various catalysts.

FIGS. 2 to 4 show results from characterization of the total conversion effluent. In FIG. 2, the selectivity for formation of $C_{5+}$ compounds is shown versus the ratio of olefins to other components in the effluent. The $C_{5+}$ selectivity is roughly a proxy for naphtha yield while the ratio of olefins to (aromatics+naphthenes+paraffins) is roughly a measure of the amount of hydrogen transfer in the reaction environment. It is noted that as a catalyst deactivates, both naphtha yield and the amount of hydrogen transfer can vary, so the type of data shown in FIG. 2 can change as a catalyst deactivates. It is believed that hydrogen transfer can result in conversion of olefins to paraffins, with corresponding production of additional aromatics. The results in FIG. 2 correspond to both results with recycle of light ends to the reactor (triangle data points) and without recycle (circle data points). As shown in FIG. 2, when recycle was not used, the catalysts without phosphorus had higher $C_{5+}$ selectivity as the ratio of olefins to other components increased. As indicated by the triangle data points, when the light olefins were recycled back to the reactor, the $C_{5+}$ selectivity was similar for the catalysts with and without phosphorus, although the $C_{5+}$ selectivity still remained higher for the catalysts without phosphorus.

The nature of the hydrogen transfer is further illustrated in FIGS. 3 and 4. In FIG. 3, the propene yield is shown as a function of the olefin ratio, while in FIG. 4 the propane yield is shown as a function of the olefin ratio. As shown in FIG. 3, the yield of propene relative to the olefin ratio is similar for both the catalysts with and without phosphorus, and with or without recycle. This likely indicates that propene is formed at an equilibrium level within the reaction environment. However, FIG. 4 shows that the amount of propane relative to the olefin ratio is substantially higher for the catalysts including phosphorus. This is believed to be the result of increased hydrogen transfer, which can cause an increased rate of saturation of propene to propane, leading to increased propane in the reaction effluent. Thus, it is believed that the higher paraffin selectivity in FIG. 4 is the result of a change in the rate of hydrogen transfer, resulting in "trapping" of some olefins as paraffins. Thus, the data in FIG. 3 and FIG. 4 does not appear to indicate a reduction in the availability of light olefins for upgrading to naphtha.

Figure 11:
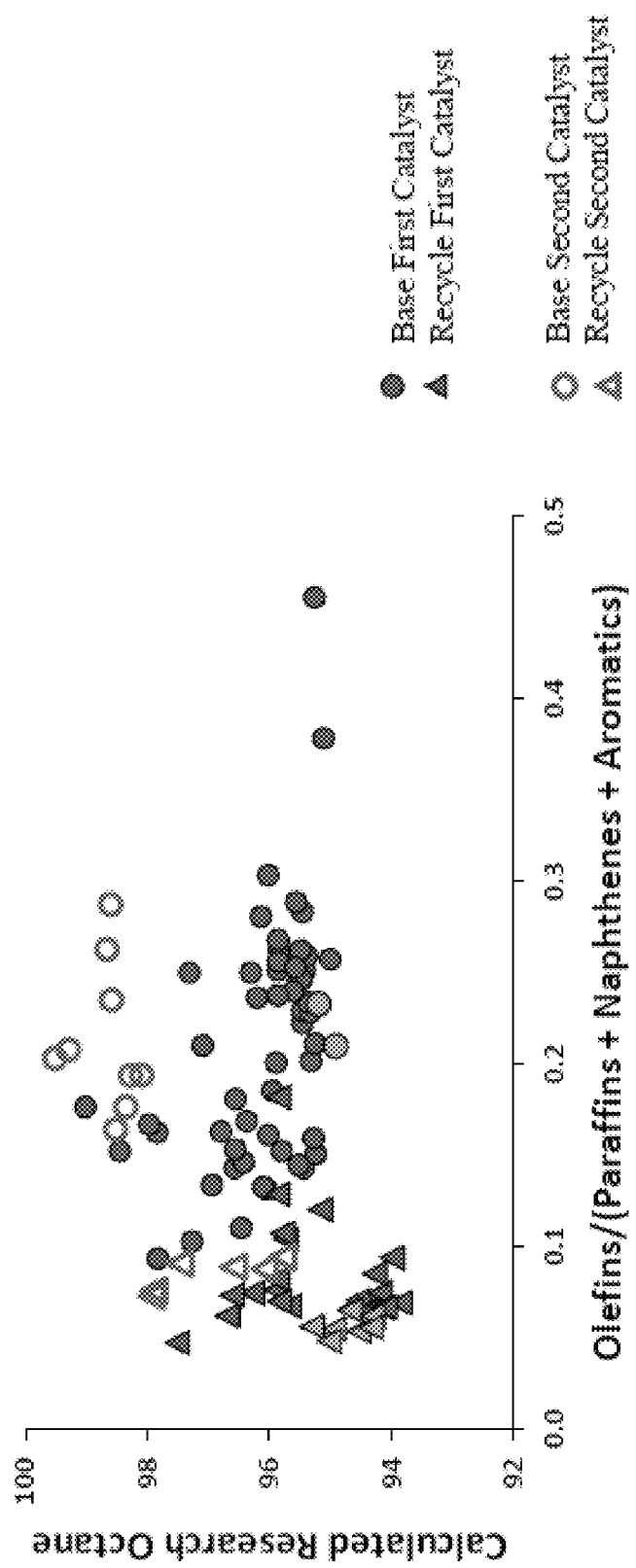
FIG. 11 shows calculated Research Octane Number versus the fraction of olefins in the total hydrocarbon product from conversion of methanol in the presence of various catalysts.

Without being bound by any particular theory, it is believed that the hydrogen transfer reaction resulting in saturation of propene to propane also results in increased formation of aromatics. This can result in increased octane for the $C_{5+}$ portion of the reaction effluent. FIG. 11 shows calculated research octane numbers that were calculated based on compositional analysis of the total conversion effluent. As shown in FIG. 11, the total conversion effluents from the second catalyst tended to have a calculated research octane that was higher than the calculated research octane for the effluents from the first catalyst. This difference in calculated research octane was more pronounced for the data points where the light ends from the total conversion effluent were not recycled, but the improved octane is still present in the recycle data points as well.

Example 2—Methanol Conversion in Fixed Bed Using P-ZSM-5

To further investigate the impact of increased hydrogen transfer on the conversion effluent during methanol conversion, a series of fixed bed tests of activity for various samples of ZSM-5 and phosphorus-enhanced ZSM-5 catalysts were performed in an isothermal micro-unit. The tests were performed at 30 psig (~200 kPa-g) of methanol, a weight hourly space velocity (WHSV) of 1.0 $hr^{-1}$, and temperatures of 340° C.-370° C.

Figure 5:
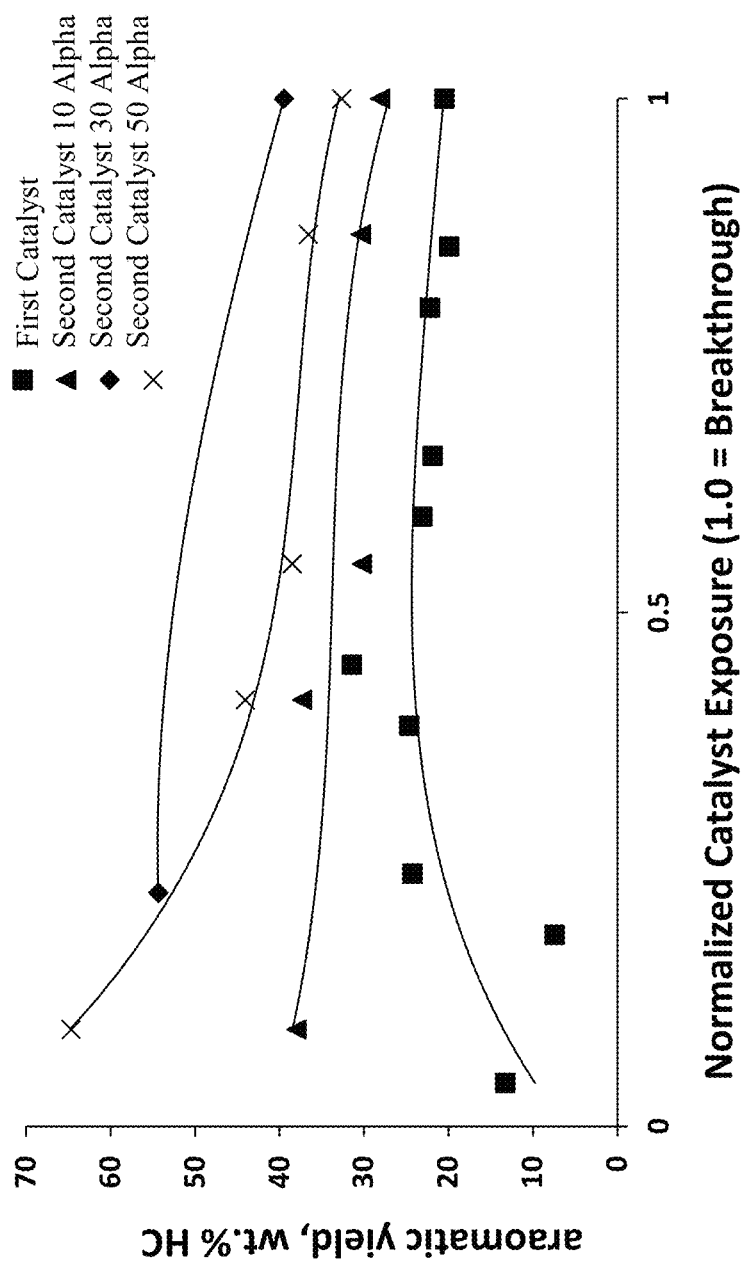
FIG. 5 shows aromatic yield versus normalized average catalyst exposure for conversion of methanol in the presence of various catalysts.

FIG. 5 shows the aromatics yield relative to the total weight of hydrocarbons in the conversion effluent versus normalized average catalyst methanol exposure at the pressure and temperature of the test. As shown in FIG. 5, the phosphorus-enhanced catalysts result in increased aromatic production in the total hydrocarbon product, leading to increased octane for the $C_{5+}$ portion. The highest aromatic yield is achieved for the catalyst with an Alpha of 30, with the catalyst having an Alpha of 50 providing similar results. The catalyst with an Alpha value of 10, which roughly corresponds to a catalyst with an equilibrium Alpha after long steaming, has lower aromatics than the catalysts with Alpha of 30 or 50, but the aromatics yield is still higher than the catalyst without phosphorus. It is noted that the aromatics yield benefit begins to be reduced as the catalyst approaches a normalized average catalyst exposure of 1.0. In additional testing, it was determined that the advantage in aromatics yield was further reduced or minimized at normalized average catalyst exposures greater than 1.0.

Figure 6:
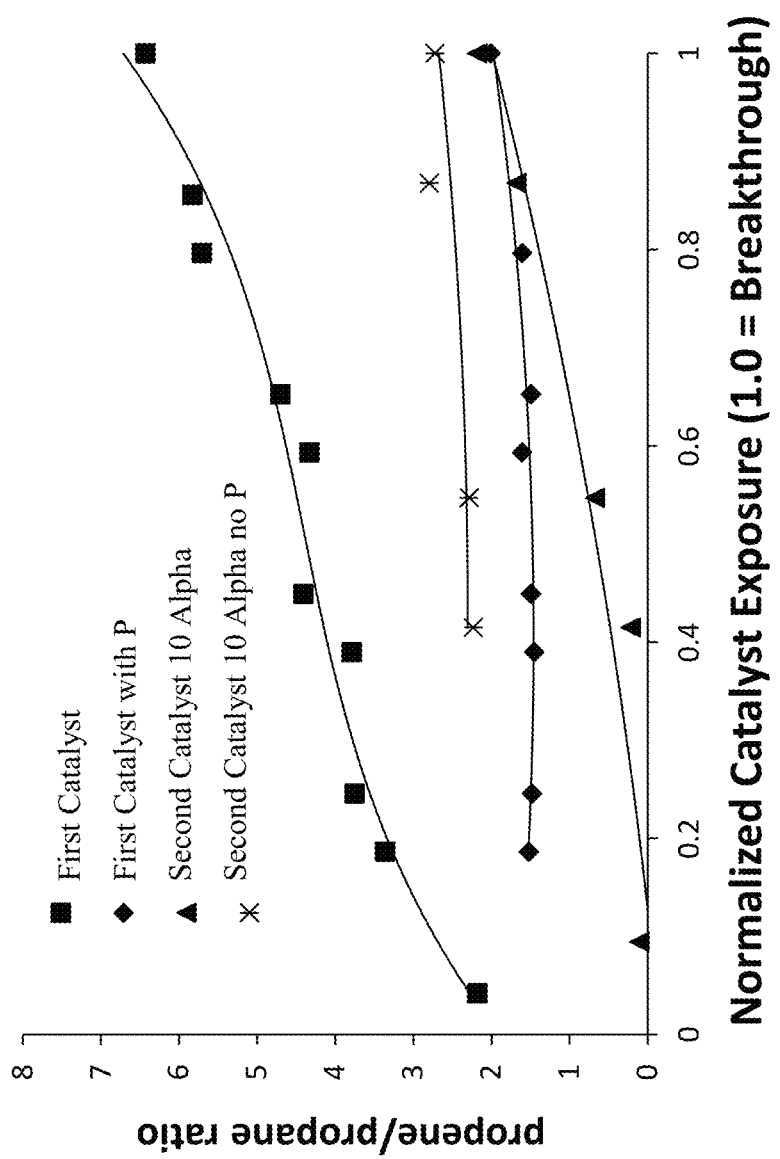
FIG. 6 shows propene to propane ratio versus normalized average catalyst exposure for conversion of methanol in the presence of various catalysts.

FIG. 6 shows that while phosphorus content provides the largest contribution to improved aromatics yield, the crystal size can also provide a contribution to improved hydrogen transfer and therefore improved aromatics yield. In FIG. 6, catalysts were made with and without phosphorus using both the smaller crystal size and larger crystal size versions of ZSM-5. The Alpha value for the larger crystal size ZSM-5 catalysts in FIG. 6 was 10 (roughly the equilibrium value). The conversion effluent generated by the various catalysts was then characterized to determine the propene versus propane ratio at various values for the normalized average catalyst exposure. As shown in FIG. 6, the presence or absence of phosphorus was the largest contributor to hydrogen transfer, as demonstrated by the phosphorus-enhanced catalysts having the lowest propene to propane ratios. But larger crystal size (greater than 100 nm) also reduced the propene to propane ratio.

Figure 7:
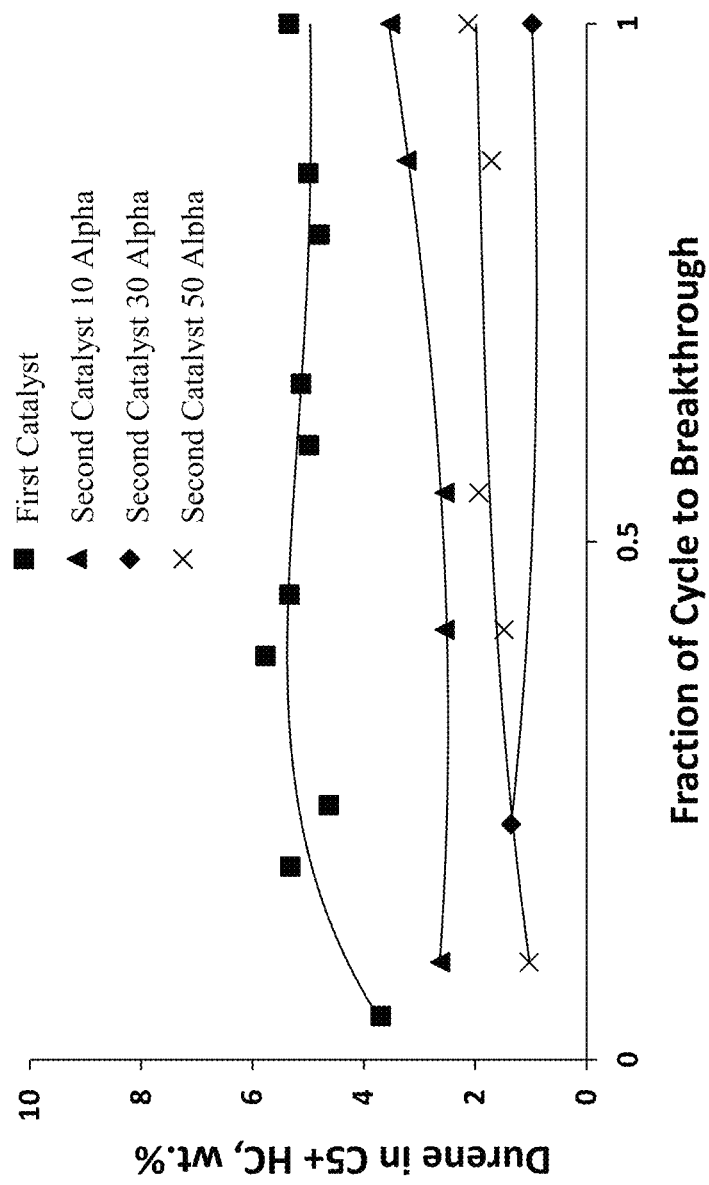
FIG. 7 shows durene yield versus normalized average catalyst exposure for conversion of methanol in the presence of various catalysts.

The impact of increased hydrogen transfer is also demonstrated by the unexpected reduction in durene content caused by the inclusion of phosphorus in the catalyst. FIG. 7 shows durene content relative to normalized average catalyst exposure for the baseline catalyst (small crystal, no phosphorus) and for phosphorus-enhanced versions of the large crystal catalyst at Alpha values of 10, 30 and 50. As shown in FIG. 7, the phosphorus-enhanced catalysts had substantially lower durene content. This is beneficial, as durene has a relatively high melting point, making it an undesirable compound in gasolines due to the potential, for example, for forming particulates that can clog fuel filters.

Example 3—Addition of Zn

Figure 8:
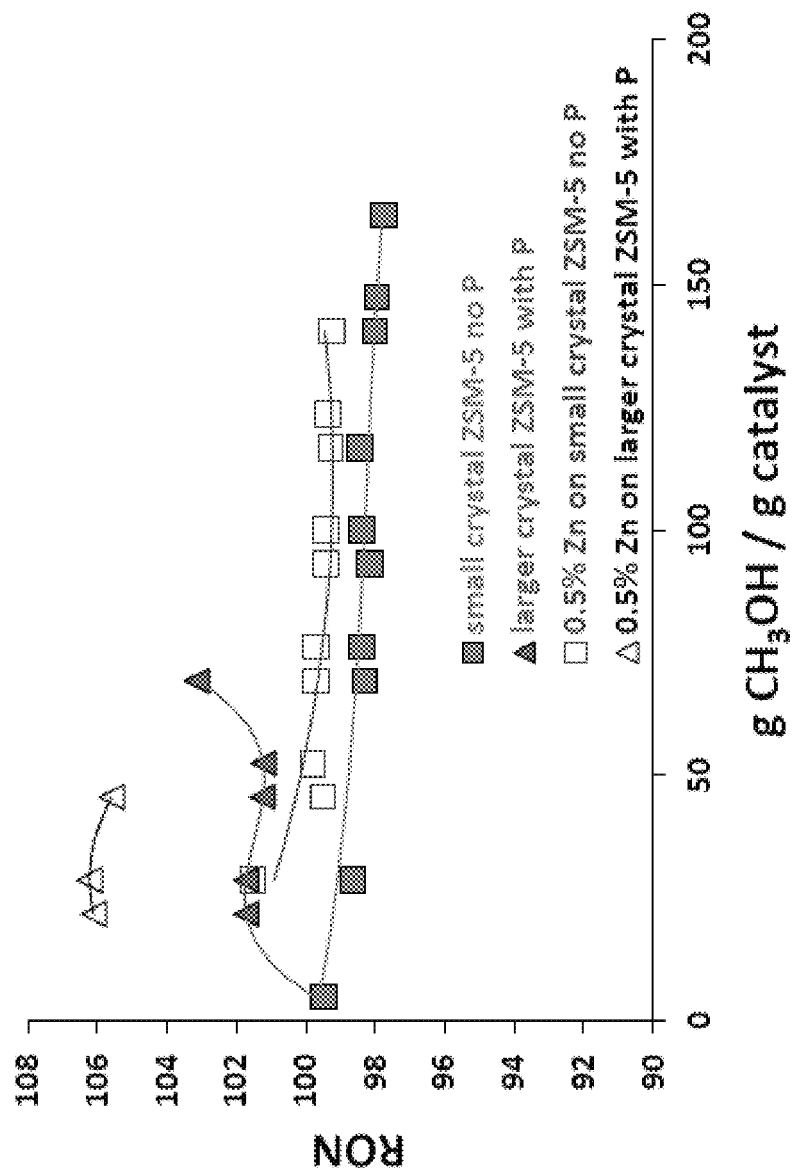
FIG. 8 shows research octane number versus normalized average catalyst exposure for the $C_{5+}$ fraction of the total hydrocarbon product from conversion of methanol in the presence of catalysts with and without supported zinc.

It has been discovered that the addition of zinc provides a synergistic benefit for improvement of octane when used in conjunction with a phosphorus-enhanced catalyst. This unexpected benefit is achieved for relatively small values of average catalyst exposure. FIG. 8 shows the impact of addition of zinc on the octane of the $C_{5+}$ portion of the conversion effluent for both the first catalyst (small crystal, no phosphorus) and the second catalyst (larger crystal, with phosphorus). As shown in FIG. 8, zinc provides a modest boost to octane for the first catalyst. An unexpectedly larger octane increase is provided when adding zinc to the second catalyst.

Figure 9:
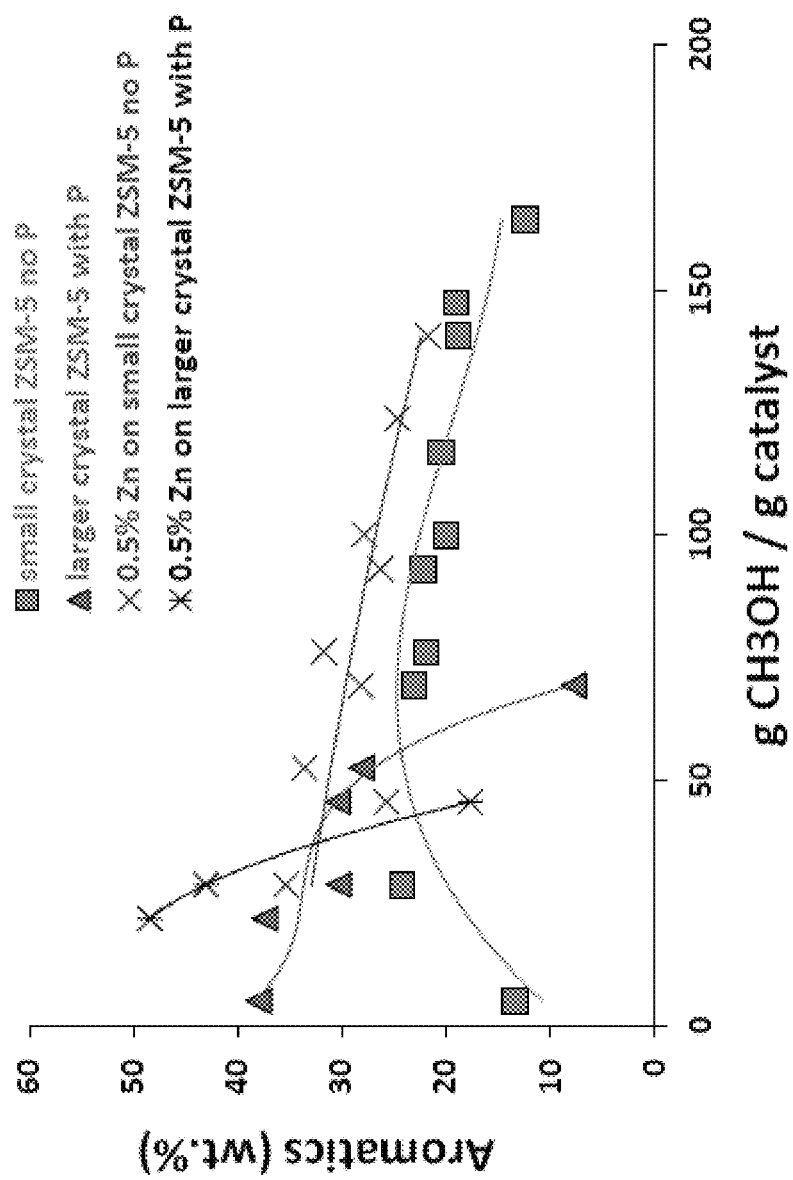
FIG. 9 shows aromatic yield versus average catalyst exposure for the $C_{5+}$ fraction of the total hydrocarbon product from conversion of methanol in the presence of catalysts with and without supported zinc.
Figure 10:
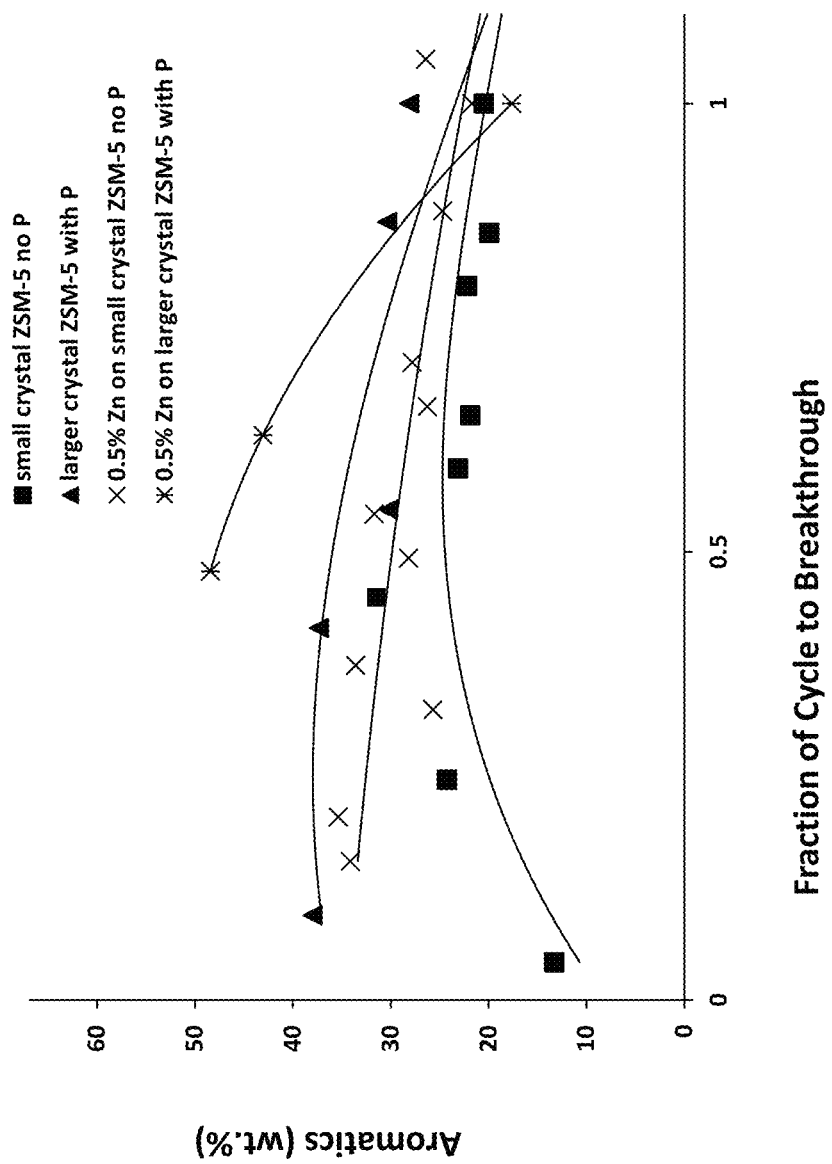
FIG. 10 shows the aromatic yield versus normalized average catalyst exposure for the $C_{5+}$ fraction for the total hydrocarbon product from conversion of methanol in the presence of catalysts with and without supported zinc.

FIG. 9 further illustrates the nature of the unexpected benefit from addition of zinc. FIG. 9 shows the aromatics selectivity for the catalysts in FIG. 8. As shown in FIG. 9, the aromatics yield for the Zn-enhanced catalysts (with or without addition of phosphorus) drops more quickly with increasing exposure to feed. However, this is due to the activity of the Zn-enhanced catalysts dropping to 99% or less at smaller amounts of oxygenate exposure than the catalysts without Zn. FIG. 10 shows data similar to FIG. 9, but plotted against normalized average catalyst exposure for methanol. As shown in FIG. 10, when plotted against normalized average catalyst exposure, the Zn-enhanced catalysts maintain the enhanced aromatics selectivity for normalized average exposure times up to 1.0. This demonstrates that using a higher regeneration rate can allow the increased octane benefit of Zn addition to be achieved in a fluidized bed type reactor/moving bed type reactor by controlling the regeneration rate of the Zn-enhanced catalyst. It is noted that when recycle is used in conjunction with the Zn-containing catalysts, the overall $C_{5+}$ yield is similar.

ADDITIONAL EMBODIMENTS

Embodiment 1

A method for forming a hydrocarbon composition, comprising: exposing an oxygenate-containing feed to conversion catalyst particles comprising 0.01 wt % to 20 wt % phosphorus on a zeolitic support under effective oxygenate conversion conditions comprising a temperature of 320° C. to 425° C., a pressure of 10 psig (~70 kPa-g) or more, and a weight hourly space velocity of 0.1 $hr^{-1}$ to 10.0 $hr^{-1}$, to form a hydrocarbon product comprising $C_{5+}$ hydrocarbons and $C_2$-$C_4$ olefins, the conversion catalyst particles comprising an average Alpha value of 8 to 15, the $C_{5+}$ hydrocarbons comprising a RON of 80 or more, the exposing comprising exposing the oxygenate-containing feed to the conversion catalyst particles in a reaction system comprising a fluidized bed reactor, a moving bed reactor, a riser reactor, or a combination thereof.

Embodiment 2

The method of Embodiment 1, wherein the exposing is performed in a reaction system, the method further comprising: removing a first portion of catalyst particles from the reaction system; and adding fresh catalyst particles to the reaction system, the fresh catalyst particles comprising an Alpha value of 8 to 100 (or 15 to 100, or 8 to 50, or 15 to 50).

Embodiment 3

A method for forming a hydrocarbon composition, comprising: exposing an oxygenate-containing feed to conversion catalyst particles comprising 0.01 wt % to 20 wt % phosphorus on a zeolitic support under effective oxygenate conversion conditions comprising a temperature of 320° C. to 425° C., a pressure of 10 psig (~70 kPa-g) or more, and a weight hourly space velocity of 0.1 $hr^{-1}$ to 10.0 $hr^{-1}$, to form a hydrocarbon product comprising $C_{5+}$ hydrocarbons and $C_2$-$C_4$ olefins, the $C_{5+}$ hydrocarbons comprising a RON of 80 or more, removing a first portion of catalyst particles from the reaction system; and adding fresh catalyst particles to the reaction system, the fresh catalyst particles comprising an Alpha value of 15 to 100 (or 15 to 75, or 15 to 50), wherein the exposing comprises exposing the oxygenate-containing feed to the conversion catalyst particles in a reaction system comprising a fluidized bed reactor, a moving bed reactor, a riser reactor, or a combination thereof.

Embodiment 4

The method of any of the above embodiments, wherein the conversion catalyst particles comprise a normalized average catalyst exposure of 1.0 or less.

Embodiment 5

The method of any of the above embodiments, wherein the conversion catalyst particles comprise an average Alpha value of 10 to 15.

Embodiment 6

The method of any of the above embodiments, wherein 40 wt % or more of the conversion catalyst particles comprise an Alpha value of 10 or less; or wherein 1.0 wt % or more of the conversion catalyst particles comprise an Alpha value of 4.0 or less; or a combination thereof.

Embodiment 8

The method of any of the above embodiments, wherein the conversion catalyst particles further comprise 0.1 wt % to 2.0 wt % Zn.

Embodiment 9

The method of claim 1, wherein the zeolitic support comprises an MFI framework, an MEL framework, or a combination thereof, the zeolitic support optionally comprising ZSM-5.

Embodiment 10

The method of any of the above embodiments, wherein the conversion catalyst particles comprise 0.1 wt % to 5.0 wt % phosphorus.

Embodiment 11

The method of any of the above embodiments, wherein the $C_{5+}$ hydrocarbons comprise an octane rating of 80 or more; or wherein the $C_{5+}$ hydrocarbons comprise a RON of 90 or more; or a combination thereof.

Embodiment 12

The method of any of the above embodiments, wherein the hydrocarbon product comprises 40 wt % or more aromatics.

Embodiment 13

The method of any of the above embodiments, wherein the oxygenate-containing feed further comprises at least a portion of the $C_2$-$C_4$ olefins.

Embodiment 14

The method of any of the above embodiments, wherein the oxygenate-containing feed comprises 90 wt % or more of methanol, dimethyl ether, or a combination thereof, relative to a weight of oxygenates in the oxygenate-containing feed.

Embodiment 15

A hydrocarbon product or a $C_{5+}$ portion of a hydrocarbon product made according to the method of any of Embodiments 1-14.

All numerical values within the detailed description and the claims herein are modified by "about" or "approximately" the indicated value, and take into account experimental error and variations that would be expected by a person having ordinary skill in the art.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for forming a hydrocarbon composition, comprising:

exposing an oxygenate-containing feed to conversion catalyst particles comprising 0.01 wt % to 20 wt % phosphorus on a zeolitic support under effective oxygenate conversion conditions comprising a temperature of 330° C. to 400° C., a pressure of 10 psig (~70 kPa-g) or more, and a weight hourly space velocity of 0.1 $hr^{-1}$ to 10.0 $hr^{-1}$, to form a hydrocarbon product comprising $C_{5+}$ hydrocarbons and $C_2$-$C_4$ olefins, the conversion catalyst particles comprising an average Alpha value of 8 to 15, the $C_{5+}$ hydrocarbons comprising a RON of 80 or more, the exposing comprising exposing the oxygenate-containing feed to the conversion catalyst particles in a reaction system comprising a fluidized bed reactor, a moving bed reactor, a riser reactor, or a combination thereof, and wherein the conversion catalyst particles comprise a normalized average catalyst exposure of less than 1.0.

2. The method of claim 1, wherein the oxygenate-containing feed further comprises at least a portion of the $C_2$-$C_4$ olefins.

3. The method of claim 1, wherein the oxygenate-containing feed comprises 90 wt % or more of methanol, dimethyl ether, or a combination thereof, relative to a weight of oxygenates in the oxygenate-containing feed.

4. The method of claim 1, wherein the conversion catalyst particles comprise an average Alpha value of 10 to 15.

5. The method of claim 1, wherein 40 wt % or more of the conversion catalyst particles comprise an Alpha value of 10 or less; or wherein 1.0 wt % or more of the conversion catalyst particles comprise an Alpha value of 4.0 or less; or a combination thereof.

6. The method of claim 1, wherein the exposing is performed in a reaction system, the method further comprising:

removing a first portion of catalyst particles from the reaction system; and adding fresh catalyst particles to the reaction system, the fresh catalyst particles comprising an Alpha value of 8 to 100.

7. The method of claim 1, wherein the conversion catalyst particles further comprise 0.1 wt % to 2.0 wt % Zn.

8. The method of claim 7, wherein the $C_{5+}$ hydrocarbons comprise an RON of 90 or more.

9. The method of claim 1, wherein the zeolitic support comprises an MFI framework, an MEL framework, or a combination thereof.

10. The method of claim 1, wherein the zeolitic support comprises ZSM-5.

11. The method of claim 1, wherein the conversion catalyst particles comprise 0.1 wt % to 5.0 wt % phosphorus.

12. The method of claim 1, wherein the hydrocarbon product comprises 40 wt % or more aromatics.

13. A method for forming a hydrocarbon composition, comprising:

exposing an oxygenate-containing feed to conversion catalyst particles comprising 0.01 wt % to 20 wt % phosphorus on a zeolitic support under effective oxygenate conversion conditions comprising a temperature of 330° C. to 400° C., a pressure of 10 psig (~70 kPa-g) or more, and a weight hourly space velocity of 0.1 $hr^{-1}$ to 10.0 $hr^{-1}$, to form a hydrocarbon product comprising $C_{5+}$ hydrocarbons and $C_2$-$C_4$ olefins, the $C_{5+}$ hydrocarbons comprising a RON of 80 or more, removing a first portion of catalyst particles from the reaction system; and adding fresh catalyst particles to the reaction system, the fresh catalyst particles comprising an Alpha value of 15 to 100, wherein the exposing comprises exposing the oxygenate-containing feed to the conversion catalyst particles in a reaction system comprising a fluidized bed reactor, a moving bed reactor, a riser reactor, or a combination thereof, and wherein the conversion catalyst particles comprise a normalized average catalyst exposure of less than 1.0.

14. The method of claim 13, wherein the conversion catalyst particles comprise an average Alpha value of 10 to 15.

15. The method of claim 13, wherein 40 wt % or more of the conversion catalyst particles comprise an Alpha value of 10 or less; or wherein 1.0 wt % or more of the conversion catalyst particles comprise an Alpha value of 4.0 or less; or a combination thereof.

16. The method of claim 13, wherein the conversion catalyst particles further comprise 0.1 wt % to 2.0 wt % Zn.

17. The method of claim 13, wherein the hydrocarbon product comprises 40 wt % or more aromatics.

18. The method of claim 13, wherein the conversion catalyst particles comprise 0.1 wt % to 5.0 wt % phosphorus.

19. The method of claim 13, wherein the $C_{5+}$ hydrocarbons comprise an RON of 90 or more.

* * * * *